United States Patent [19]
Everett et al.

[11] Patent Number: 5,649,924
[45] Date of Patent: Jul. 22, 1997

[54] MEDICAL DEVICE FOR IRRADIATION OF TISSUE

[75] Inventors: Royice B. Everett, Edmond, Okla.; George M. Acosta, Long Beach; Hany M. G. Hussein, Costa Mesa, both of Calif.

[73] Assignee: Trimedyne, Inc., Irvine, Calif.; a part interest

[21] Appl. No.: 370,673

[22] Filed: Jan. 10, 1995

Related U.S. Application Data

[63] Continuation of Ser. No. 96,478, Jul. 22, 1993, Pat. No. 5,380,317, which is a continuation of Ser. No. 460,843, Jan. 31, 1990, Pat. No. 5,242,437, which is a continuation-in-part of Ser. No. 205,218, Jun. 10, 1988, abandoned.

[51] Int. Cl.$^6$ ................................................. A61B 17/32
[52] U.S. Cl. ................................................. 606/15; 607/89
[58] Field of Search ...................... 606/7, 13–17; 607/88, 89

[56] References Cited

U.S. PATENT DOCUMENTS

| | | | |
|---|---|---|---|
| 3,821,510 | 6/1974 | Muncheryan | 219/121 |
| 4,207,874 | 6/1980 | Choy | 128/6 |
| 4,279,246 | 7/1981 | Chikama | 128/6 |
| 4,445,892 | 5/1984 | Hussein et al. | 604/101 |
| 4,449,528 | 5/1984 | Auth et al. | 128/303.1 |
| 4,646,737 | 3/1987 | Hussein et al. | 128/303.1 |
| 4,740,047 | 4/1988 | Abe et al. | |
| 4,773,413 | 9/1988 | Hussein et al. | |
| 4,860,743 | 8/1989 | Abela | |

FOREIGN PATENT DOCUMENTS 2826383A 12/1979 Germany.

OTHER PUBLICATIONS

Daniell et al., "Photodynamic Ablation of the Endometrium With the Nd:YAG Laser Hysteroscopically as a Treatment of Menorrhagia", *Colposcopy & Gynecologic Laser Surgery*, vol. 2, No. 1 1986.

Goldrath et al., "Laser photovaporization of endometrium for the treatment of menorrhagia", *Am J. Obstet. Gynecol.*, vol. 140, No. 1, p. 14, May 1, 1981.

*Primary Examiner*—Max Hindenburg
*Attorney, Agent, or Firm*—Olson & Hierl, Ltd.

[57] ABSTRACT

A medical device applies localized heat to a site in a patient's body by irradiation with light and by conduction. The device includes a radiant energy transmitting conduit, typically an optic fiber, that carries radiant energy, typically high intensity light such as laser, into a body cavity, typically the uterus, from an energy source, typically a laser source, that is located exterior to the body. At the operative head of the device within the body cavity a portion of the transmitted radiant energy is absorbed and converted to heat. This heat is radiated or conducted from the device head substantially omnidirectionally in order to aid in destruction of tissue. Meanwhile, another portion of the transmitted radiant energy is emitted through an aperture in the device head as light energy suitable for more localized and intense heating and destruction of tissue or other organic matter. This light emission is preferably directionally transverse to an elongate body of the device head. The device is suitable for selective destruction of tissue or other matter by highly localized heating.

21 Claims, 5 Drawing Sheets

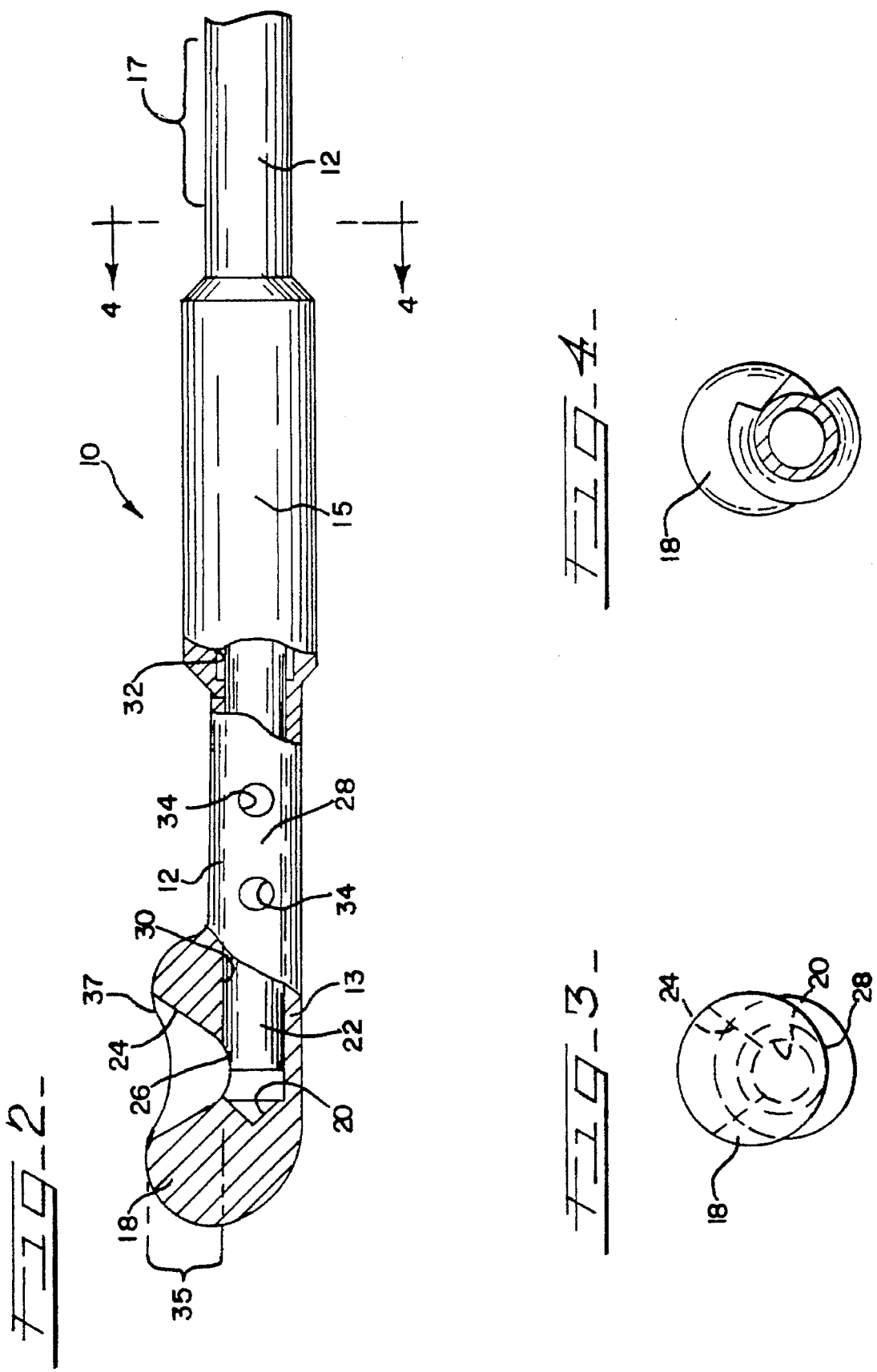

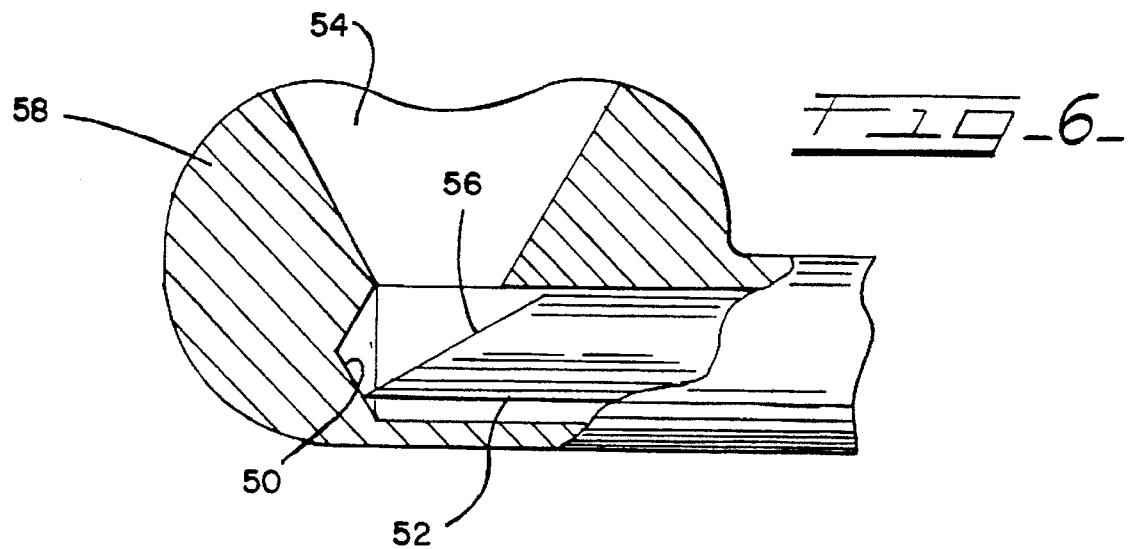
FIG-6-
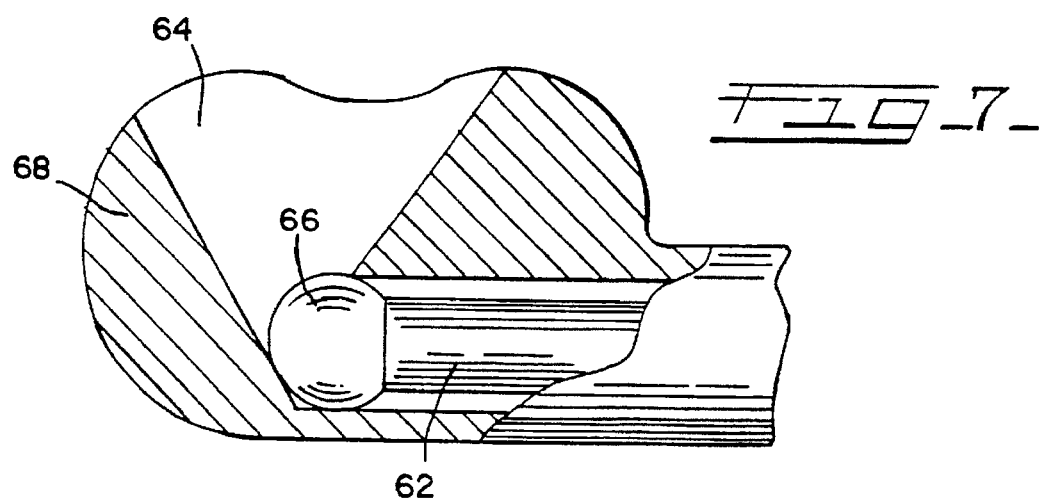
FIG-7-
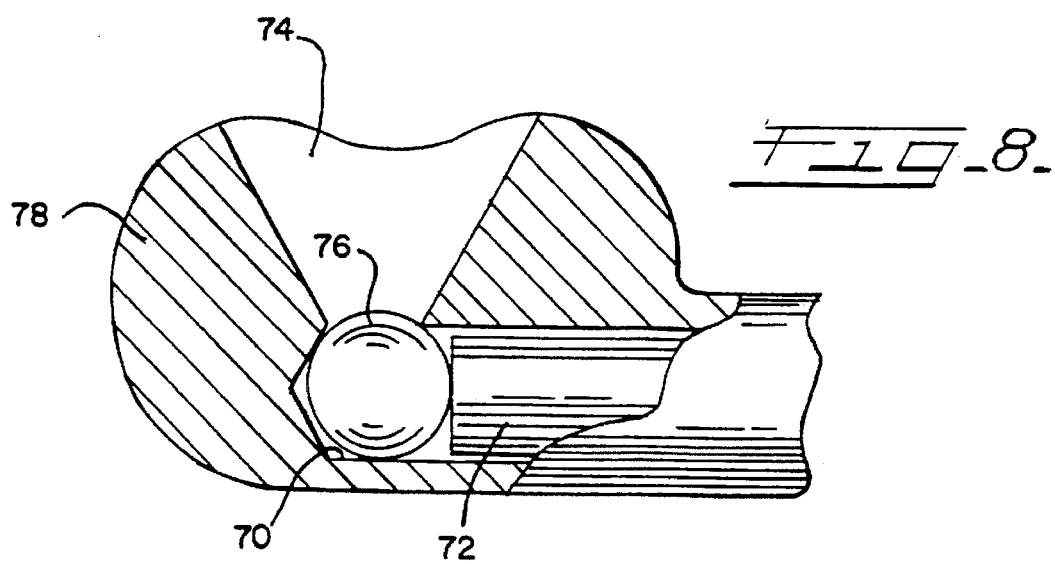
FIG-8-

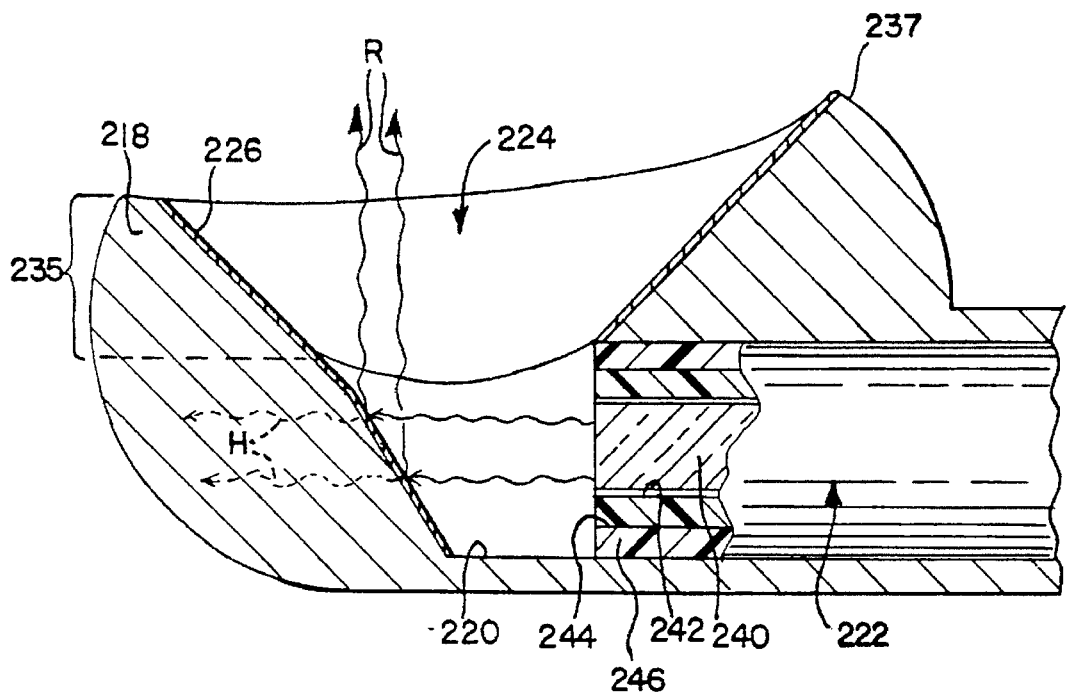
FIG_9_
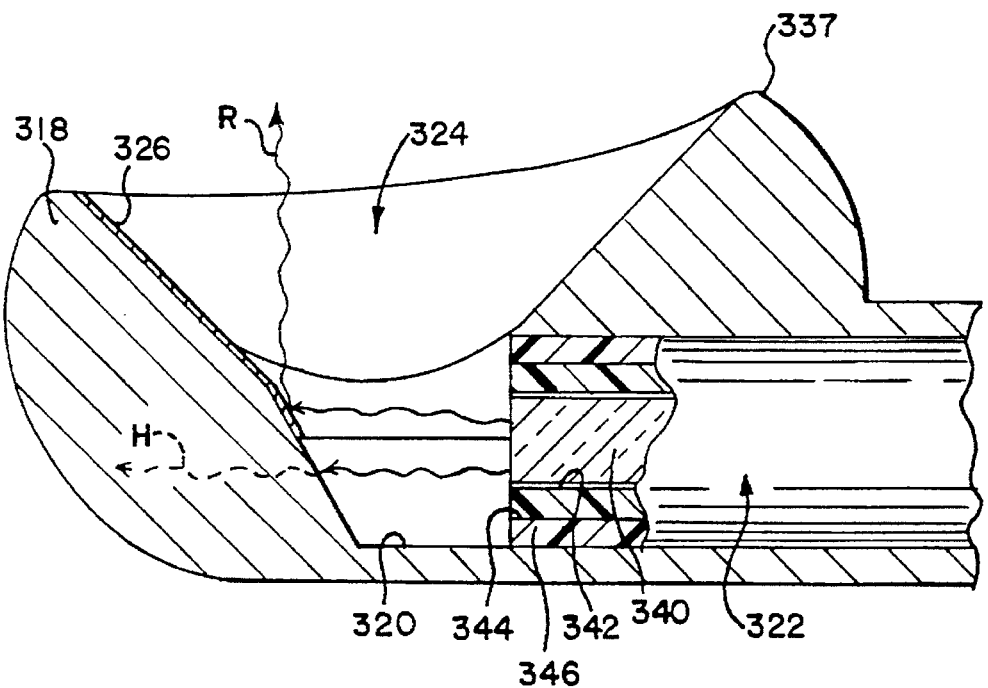
FIG_10_

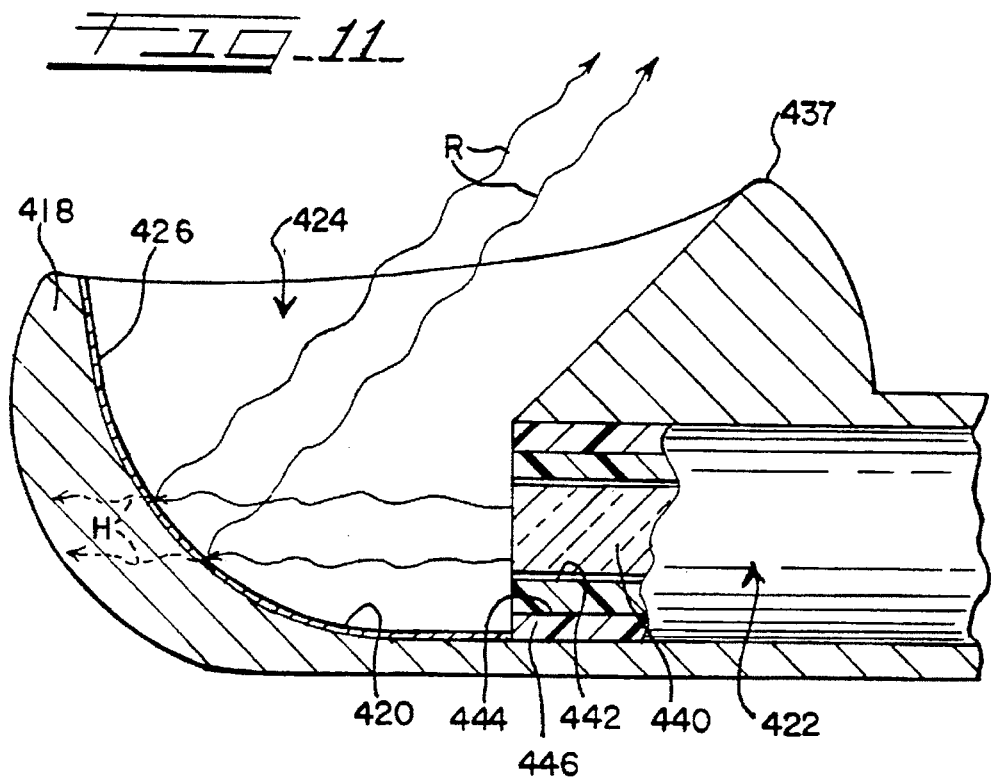
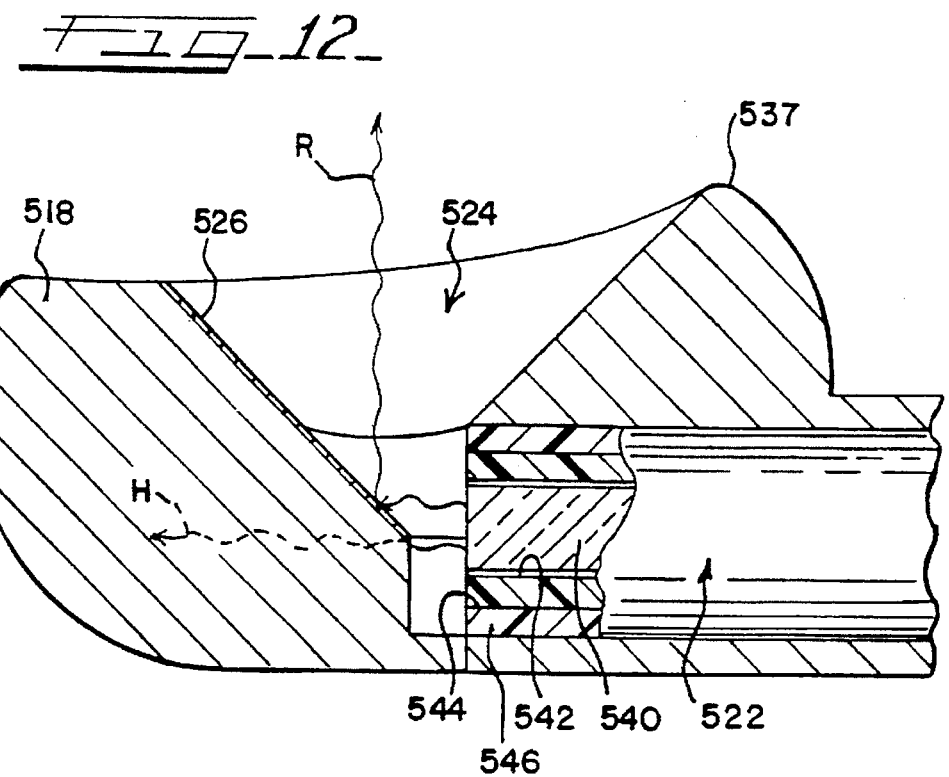

MEDICAL DEVICE FOR IRRADIATION OF TISSUE

CROSS-REFERENCE TO RELATED APPLICATIONS

This application is a continuation of U.S. Ser. No. 08/096,478, filed on Jul. 22, 1993 and now U.S. Pat. No. 5,380,317, which in turn is a continuation of U.S. Ser. No. 07/460,843, filed on Jan. 31, 1990 and now U.S. Pat. No. 5,242,437, which is a continuation-in-part of U.S. Ser. No. 07/205,218, filed on Jun. 10, 1988, abandoned.

TECHNICAL FIELD OF THE INVENTION

The present invention relates to medical devices and procedures for applying localized heat to a site in a patient's body, particularly for purposes such as the excising of tissue or deposits, or the cauterizing or destruction of tissue.

BACKGROUND OF THE INVENTION

Localized heat applied to a site in a patient's body has often been used to Cauterize a lesion in order to stop bleeding. Localized heat can also be used to alter, remove, or destroy tissue in a patient's body. One example of the medical use of localized heating is in the treatment of a bleeding ulcer. An endoscope is inserted through a patient's esophagus to view the bleeding site and to guide an electric powered heating element to contact the site and cauterize the bleeding. Another example is the use of localized heating to remove neoplastic pulmonary tissue. Still another example is the use of such heating to cauterize the endometrium.

Unfortunately, electric heating elements can be both difficult to manipulate and slow heating. The heating rate and maximum sustainable temperature are limited by the electric current available to the element. The available current in turn is limited by the size of the wires leading to the element. Wire size limits access to body sites for two reasons: larger wires cannot be inserted into small areas, and increased wire size typically causes a loss of flexibility.

The electric current passing through the wires also limits the regions in the body in which such a device can be used. The current presents a threat of an electric shock to the patient. The electric field generated by flowing current can also have undesirable effects. One region where such an electric field could possibly be life threatening is in the heart.

One electrically heated medical device in which the end of an endoscope is heated to avoid dew forming on a window is shown in U.S. Pat. No. 4,279,246 to Chikama. That device heats the window to about body temperature to prevent dew formation. However, due to the design of the device, the heat generated on the window is limited to about body temperature and therefore cannot be used to alter or destroy tissue.

Another electrically heated medical device that becomes sufficiently hot so as to cauterize tissue is shown in U.S. Pat. No. 4,449,528 to Auth et al. A miniaturized, endoscopically deliverable thermal cautery probe is used to cauterize internal vessels. The probe is applied to tissues cold, and a large number of electric heating pulses of equal energy are then applied to an internal heating element within the probe. The probe's internal heating element is in direct thermal contact With an active heat-transfer portion that has a low heat capacity. The low heat capacity of the heat-transfer portion insures quick heating and subsequent cooling, thereby adequately coagulating tissue while minimizing heat penetration and resulting tissue damage.

Because of the difficulties with electrical heating, medical devices, systems and methods have been developed for applying localized heat that is generated otherwise than by routing an electric current to a site in a patient's body. The localized heat so generated can be used for several purposes. For example, it may be used to cauterize a lesion to stop bleeding, to remove a clot, or to remove an arteriosclerotic deposit from a blood vessel. The localized heat can also be used to create an open channel in a previously occluded blood vessel.

One medical device not employing electrical current for heating is described in U.S. Pat. No. 4,207,874 to Choy which discloses a laser tunneling device used to locate, analyze, illuminate and destroy obstructions in a lumen such as a blood vessel. The device includes a fiberoptics bundle in a flexible conduit that is insertable into the blood vessel. The conduit includes a connection to a suction source at one of its ends, a valved means of controlling the application of suction which also functions to control the injection of locating material, and a connection to the fiberoptics bundle. The fiberoptics bundle is divided into an illuminating source bundle portion, a viewing bundle portion and a laser bundle portion. The device functions to remove obstructions in tube structures of both biological and non-biological types by insertion of the conduit sheathed device into the tube structure in a position distal to the obstruction.

Still a further prior medical device contemplates use of a single fiberoptic light transmission path within a medical catheter device to be either a viewing system, a laser light transmitting system, or a combination of both. In U.S. Pat. No. 4,445,892 to Hussein et al., a dual balloon catheter device is shown to have two spaced and expandable balloons for occluding a segment of a blood vessel. An optic system is used in the segment for viewing or for delivering laser light. Both the viewing and the laser light delivery are through a circumferential window within the tubular structure of the catheter.

U.S. Pat. No. 4,646,737 to Hussein et al., describes a device that includes a heat-generating element mounted on the distal end of an elongated electromagnetic energy transmitting conduit or member. A preferred conduit is a single flexible quartz optical fiber. Electromagnetic energy in the form of visible light from an intense light source, such as a laser, is transmitted through the conduit and is emitted onto a light-receiving surface of the heat-generating element. The light is converted by the element to heat. The heated element is then placed in contact with material in a patient's body such as a clot, deposit or tissue. The heated elements alter the material by melting, removing or destroying it. The heat-generating element preferably has a rounded exterior surface end. It is typically retained on the conduit by a locking means, such as by a ridge on the element that is received in a complementary groove on the conduit.

Still other prior medical devices tunnel and cut bodily tissue and other material within the body by direct application high intensity, typically laser, light that is typically conducted through fiberoptics. Laser devices—the acronym "laser" indicating light amplification by the stimulated emission of radiation—are well known. Briefly, a laser device operates by using an intense source to cause ions to become inverted with respect to their normal energy distribution. The tendency of such ions is to relax to a so-called "ground state" (a normal distribution), and in so doing to stimulate inversion of other ions within the same wavelength. A synchronized output is promptly achieved wherein the ion's relaxations from an inverted energy state transpire in unison. A massive output of energy is thereby obtained. The output wavelength is determined by the difference between the energy level from which the ions relax and the ground state energy level which the relaxed ions assume.

The medical device shown in U.S. Pat. No. 3,315,680 to Silbertrust et al., describes a cauterizer using fiberoptic techniques to conduct ordinary and laser light in a medical application. U.S. Pat. No. 3,821,510 to Muncheryan shows the use of a laser system which accommodates fluid flow to control the temperature of the work area.

German Patent No. 2,826,383 to Eichler et al., shows a tubular probe for laser surgery that is placed against or inserted in tissue. In one embodiment, an end piece having an absorbent surface is heated by the beam while it is in contact with the tissue, thereby heating the tissue. Alternatively, in another embodiment, the end is transparent and permits the laser beam to pass through the end in order to radiatively heat the tissue.

These various types of prior medical devices do not permit that tissue destruction using the lateral direction of high intensity radiated light and using radiated and/or conducted heat should be performed closely proximately, or simultaneously, in time. This can be very useful when it is desired to destroy large surface areas of tissue to a substantial depth.

For example, a surgical procedure referred to as "endometrial ablation" has been recently developed as an alternative to hysterectomy for treatment of excessive uterine bleeding. In this procedure, an Nd:YAG laser is used to destroy the entire endometrium lining the uterus. An optical fiber is inserted in the uterus by means of a hysteroscope to conduct the laser energy to the endometrium. With the aid of a parallel optical viewing fiber of the hysteroscope, the end of the laser-transmitting fiber is slowly moved across the surface of the endometrium so that the laser energy penetrates and destroys the endometrium which is on the order of three millimeters thick. Typical prior art procedures have utilized a bare optical fiber for transmitting the laser energy. Two techniques have been developed. By one technique, the end of the bare optic fiber is actually touched to the endometrium. By a second technique, generally referred to as "blanching", the bare tip of the optic fiber is held several millimeters away from the endometrium. These techniques are generally described in Daniell et al., "Photodynamic Ablation of the Endometrium With the Nd:YAG Laser Hysteroscopically as a Treatment of Menorrhagia", *Colposcopy & Gynecologic Laser Surgery*, Vol. 2, No. 1, 1986; Mackety, "Alternative to Hysterectomy: Endometrial Albation by Laser Photovaporization", *Today's OR Nurse*, Vol. 8, No. 4; and Goldrath et al., "Laser photovaporization of endometrium for the treatment of menorrhagia", *Am. J. Obstet. Gynecol.*, Vol. 140, No. 1, page 14, May 1, 1981.

Some surgeons prefer the "blanching" technique because it is believed to create fewer complications. There is less danger of mechanical perforation of the uterus. There is less actual vaporization and cutting of the endometrial tissue and accordingly less fluid absorption thereby.

It is difficult, however, to treat the side walls of the uterus by "blanching" due to lack of room to maneuver the optic fiber so as to direct it toward the side walls. Thus a touching or dragging technique has necessarily been utilized during those portions of the procedure. In addition to being unable to direct the laser energy directly at the side wall of the endometrium, this touching of the fiber tip to the endometrium is, as mentioned, considered undesirable by some surgeons.

Furthermore, with the touching technique, and to a lesser extent with the blanching technique, there is always the problem of completely treating the entire endometrium without missing small areas here and there.

Accordingly, it would be desirable if a medical device were available which would permit more of the laser energy to be directed transversely from the optical fiber toward the side wall of the endometrium. It would further be desirable to maintain some suitable spacing between the tip of the optic fiber and the endometrium. Also, it is desirable that heat be conductively applied to the endometrium while simultaneously directing the laser energy to a more localized spot thus better insuring destruction of the entire surface of the endometrium.

It would additionally be useful if the operative excising and cauterizing head of the device were to somehow be directional, as well as necessarily controllable, in one or both of its light radiation and/or its-conductive heating effects. A preferred operational direction of the device, operative head for either the lateral transmission of light or the conductive heating of tissue would permit that one effect could be maximized over the other by action of the surgeon's positioning and orientation of the device's operative head within the body cavity. Furthermore, a device exhibiting a preferred directionality would presumably exhibit some safe orientation in which orientation the device's operative head would not be prone to destroy and/or burn the lining of the body cavity within which it was situated.

SUMMARY OF THE INVENTION

The present invention is embodied in a medical device for locally applying plural forms of energy to a selected body site, and in a method of so applying such energy. In accordance with the apparatus and method aspects of the invention, laser energy transmitted along a fiber optic may be apportioned so that a portion of the transmitted energy exits the medical device as a laser beam while the remainder is converted to heat energy. In this manner, both laser energy and conductive heat energy may be applied substantially simultaneously to the body site for performing a medical procedure.

The apparatus aspect of this invention contemplates an elongated, laser energy transmitting conduit that is provided with a beam-splitting means at its distal end and is optically coupled at its proximal end to a laser energy source. A hollow, apertured bulbous element capable of converting laser energy into heat is mounted on the distal end of the laser-transmitting conduit. The bulbous element defines a cavity within which the distal end of the conduit is received. The bulbous element also defines an aperture that communicates with the cavity. The defined aperture is positioned vis-a-vis the conduit so that it is to one side of the laser energy path that enters the aforementioned cavity but is in registry with a laser energy beam generated by the beam-splitting means. In this manner, a portion of the laser energy transmitted by the conduit is converted into heat while the remainder of the transmitted laser energy exits from the bulbous element via the aperture as a laser energy beam along a path that is different from the laser energy path entering the cavity.

The cavity within the bulbous element is typically a simple bore. The defined aperture is in the shape of a wedge, trough, cone, paraboloid or other surface proceeding from a generally wider opening at the surface of the bulbous element to a generally narrower apex that intersects the bore. The beam-splitting means is preferably a reflective surface situated within the cavity so as to intersect some portion of a laser energy bean emitted from the distal end of the laser-transmitting conduit, and so as to reflect a portion of the intercepted beam through the aperture to exit the bulbous element while a remaining portion penetrates the bulbous element, producing heat. The beam-splitting means may alternatively be realized by removing a portion of a light reflective cladding, or surrounding reflector, to the light-transmitting conduit, thereby allowing an escape of laser light energy from the bulbous element via the aperture.

A method aspect of this invention contemplates the introduction of the present apparatus or device into, for example, a body cavity or lumen of a patient and thereafter irradiating a selected body site with a laser energy beam while applying heat at a relatively lower energy density to the body site by conduction utilizing the bulbous element. In this manner coagulation, vaporization, as well as cutting can be effectively performed at the body site.

The laser energy used by the medical device in accordance with the present invention may be infrared (IR) and excimer laser light as well as visible laser light. Various suitable energies are produced by $CO_2$, Argon, Nd:YAG, excimer and other types of lasers. Particularly when the beam-splitting means of the device is implemented as a reflective surface of gold (Au), the device is very effective in providing both conductive and heat energy for a range of laser radiation frequencies, types, and energies.

Numerous other advantages and features of the present invention will be readily apparent to those skilled in the art from the following detailed description of the preferred embodiment of the invention, the drawings, and the appended claims.

BRIEF DESCRIPTION OF THE DRAWINGS

FIG. 2 is an enlarged side view, partly in section, of the distal end portion of the medical device of FIG. 1.

FIG. 3 is an enlarged end view of the distal end portion of the medical device of FIG. 1.

FIG. 4 is an enlarged cross-sectional view of the distal end portion of the medical device, taken along PLANE 4—4 in FIG. 2, with a portion broken away to show additional detail.

FIGS. 6–12 are similar to FIG. 5 and illustrate alternative embodiments of the present invention.

DESCRIPTION OF THE PREFERRED EMBODIMENT

Figure 1:
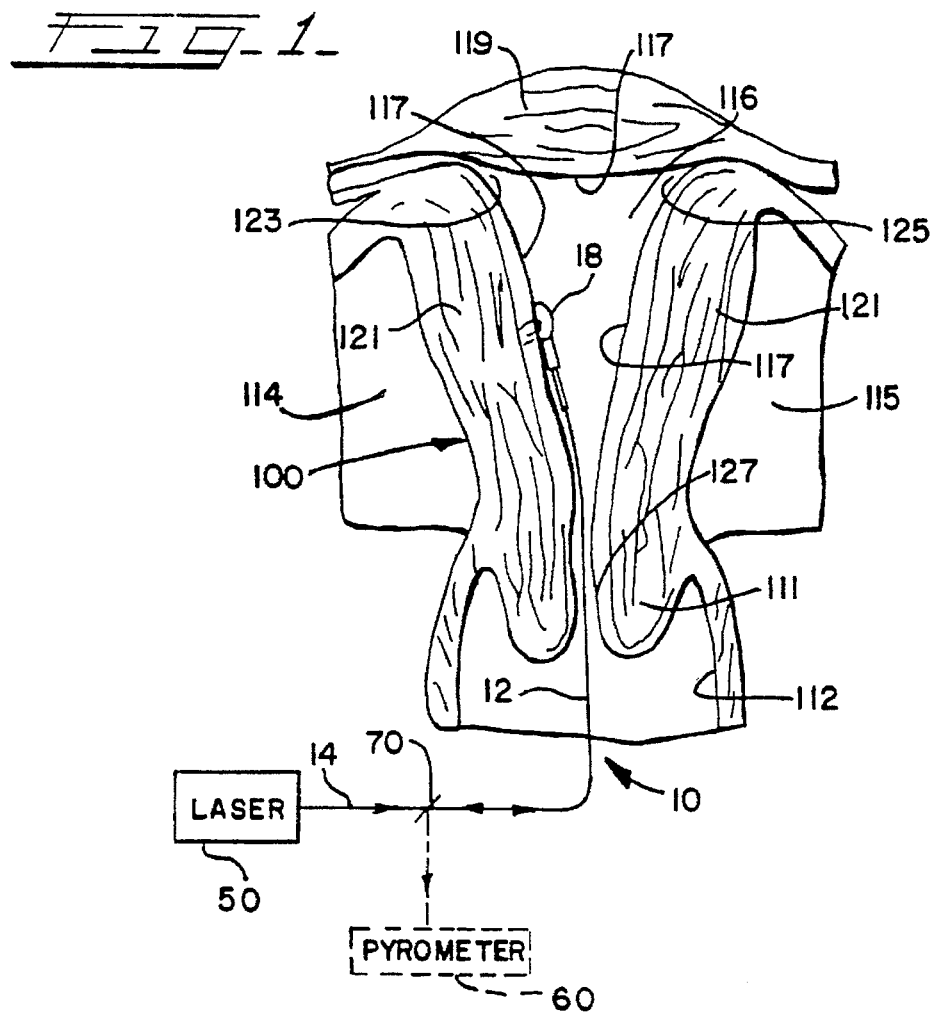
FIG. 1 is a schematic view of a system including a medical device embodying the present invention in use within a human uterus.

While the present invention can be embodied in many different forms, there is shown in the drawings, and described in detail, a preferred embodiment of the invention. The present disclosure is an exemplification of the principles of the invention and is not intended to limit the invention to the embodiment illustrated.

The present invention is a medical device for delivering and applying localized heat as well as a laser beam to a site upon, or more typically in, a patient's body. The applied energy can be used to selectively stop bleeding, or to remove or alter a material such as tissue or deposit in or on the body by vaporization, or to make an incision. The material being altered can be any solid or semi-solid substance found in or on the body including living tissue (including cancerous tissue) or deposits such as clots, fat or arteriosclerotic plaque. A particularly useful application of the invention is the destruction of the endometrium lining the uterus.

Referring to FIG. 1, medical device 10 embodying the present invention is shown positioned within the uterus 100 of a human female patient. Device 10 comprises hollow, apertured bulbous element 18 positioned within uterine cavity 116 near endometrium 117. The endometrium 117 is a thin layer of tissue lining the entire uterine cavity 116 which is defined by an upper fundus 119 and a somewhat cylindrical side wall 121. The side wall 121 can generally be defined as extending from the tubal ostia 123 and 125 down to the internal cervical os 127.

Bulbous element 18 is mounted on the distal end of elongated, laser energy transmitting conduit such as fiber optic 22 which, in turn, is optically coupled at its proximal end 14 to laser energy source 50. Optionally, a pyrometer 60 is provided at the proximal end region of device 10 for measuring the temperature of bulbous element 18. To that end, a reflected beam from bulbous element 18 is conducted to pyrometer 60 utilizing a beam-splitting means 70 such as a partial mirror, a rotating mirror, or the like.

Device 10 is inserted as part of a hysteroscope (not shown) into uterus 100 via vaginal canal 112 and through the internal cervical os 127 of cervix uteri 111 using appropriate dilation procedures as will be described in greater detail hereinbelow. The body or side wall 121 of uterus 100 is supported by broad ligaments 114 and 115.

An enlarged view of the distal end portion of device 10 is shown in FIG. 2. Bulbous element 18 defines an internal cavity 20 within which is slidably received the distal end of fiber optic 22 which serves as the laser energy transmitting conduit. A clearance is provided between the distal end of fiber optic 22 and cavity 20 to accommodate differences in thermal expansion that may be encountered upon the heating of bulbous element 18. Bulbous element 18 also defines aperture 24 that communicates with cavity 20 and provides an exit passageway for a laser energy beam diverted from the laser energy path of the laser energy entering cavity 20 via fiber optic 22. Diversion of the laser energy beam is achieved by beam-splitter means 26 which in one embodiment is a concave side portion of fiber optic 22 with laser light reflecting cladding removed therefrom. The beam splitter means 26 can also be a rounded end of fiber optic 22 without a reflective cladding, or a separate lens, e.g., a sapphire lens, positioned at the terminus of fiber optic 22, that reshapes and redirects the laser beam.

The beam splitter means may still further be a reflective surface, or mirror, on the wall of cavity opposite to the distal end of fiber optic. The reflective surface may be positioned so as to intercept all or part of the laser energy beam emitted from the distal end of fiber optic, and may be of varying reflective efficiency so as to reflect substantially all or only part of the intercepted laser energy beam. The reflective surface may be varied in its position, size, and/or efficiency to adjust the relative level of energy converted into heat versus that which exits from the bulbous element 18 as a laser energy beam.

The bulbous element 18 can be described as having a closed distal end wall (also designated by the identifying number 18 in FIG. 2) blocking any transmission of a laser energy beam distally from bulbous element 18 coaxial with the laser energy path at the distal end of conduit 22. The aperture 24 can be described as being located proximally from this closed distal end wall.

The operation of various embodiments of the beam-splitter means will be described in greater detail hereinbelow.

The internal cavity 20 of bulbous element 18 exhibits features 32–34 that facilitate the reception and clenched retention of bulbous element 18 upon fiber optic 22. The fiber optic 22 generally has a total exterior diameter or transverse dimension of about one (1) millimeter or less. Nonetheless, it generally has sufficient rigidity both to be pushed into a narrow, complementary sized, bore region 30 of cavity 20. The fiber optic 22 is facilitated in being guided into a tight fit within narrow bore region 30 by guidance accorded the fiber optic 22 in large bore region 32 to cavity 20.

When inserted to the indicated depth within bore regions 30, 32 of cavity 20, and properly rotated so that beam-splitter means 26 is properly aligned to aperture 24, the fiber optic 22 may be inspected through holes 34 defined in the sidewall of stem 12 connected to bulbous element 18. Holes 34 also provide a vent means that serves to relieve any pressure that may be generated within the bulbous element 18 due to gas expansion or vaporization of liquid as element 18 is heated. Additionally, holes 34 reduce the cross-sectional area available for heat transmission along the outer sheath 13 of hollow stem 12 unitary with bulbous element 18. Outer sheath 13 is further provided with a thermal expander section 15 which is an enlarged cylindrical segment unitary with stem 12 that serves to accommodate thermal expansion of stem 12 as bulbous element 18 is heated.

Fiber optic 22 is secured to stem 12 in the region 17 immediately behind or abaft of thermal expander section 15, preferably by crimping or like mechanical securement means. Alternatively, or in addition, a heat resistant adhesive such as an epoxy glue may be used.

An enlarged distal end view of the medical device 10 is shown in FIG. 3. The aperture 24 shown in FIGS. 2 and 3 is preferably of a sophisticated contour. It subtends an arcuate portion of the circumference of bulbous element 18, and of the circumference of fiber optic 22. This arcuate portion is typically less than one quadrant of 90°. The overall aperture 24 is substantially in the shape of a frustum. The wide base of the frustum is disposed to the exterior of the bulbous element 18. The truncated apex of the frustum is abutting the distal end region of the light-transmitting fiber optic 22 at the position of its beam-splitter means 26. Because the cross section of aperture 24 is substantially circular, it may be accurately described as being substantially frustoconical in shape.

There is a spacing or standoff 35 defined between fiber optic 22 and an outer surface 37 of bulbous element 18 which will be contacted with the endometrium. This distance 35 is on the order of the diameter of fiber optic 22, i.e., 1 millimeter.

As seen in FIGS. 2, 3 and 4, the portion of bulbous element 18 having the aperture 24 defined therein protrudes eccentrically from probe 18 relative to the longitudinal axis of conduit 22. It is this eccentrically protruding probe portion which defines the standoff distance 35.

An enlarged cross-sectional view of the bulbous element taken along plane 4—4 shown in FIG. 2 is shown in FIG. 4. The axial offset between the distal head and the proximal shank regions of bulbous element 18 facilitates maneuvering of the prominent distal head region of the element 18 into proximity or contact with tissue while, at a preferred angular orientation of use, the distal shank region of the element 18 remains more remote from the tissue. Tissue selective contact with only proximal or distal regions of bulbous element 18 cannot be totally assured when the device 10 is used in tight bodily cavities such as the uterus 100 (shown in FIG. 1), but the axial offset to bulbous element 18 promotes that its distal head region may be selectively placed in contact with the tissue.

Further, the spacing 35 maintained between the distal end of fiber optic 22 and the tissue being treated minimizes the disadvantages mentioned that often result from actual touching of the fiber optic 22 to the endometrium.

Figure 5:
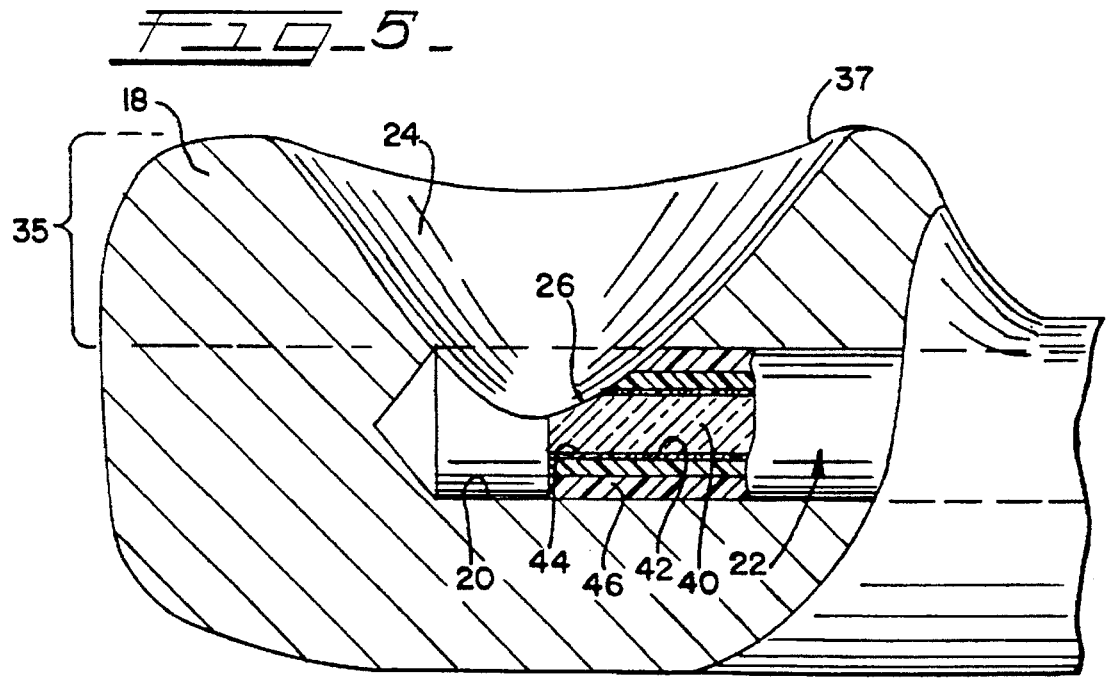
FIG. 5 is an enlarged cross-sectional detail view of the distal end portion of the medical device of FIG. 1.

An enlarged cross-sectional view of the distal head region of bulbous element 18 is shown in FIG. 5. The fiber optic 22 includes a core 40 surrounded by cladding 42. The internal reflection caused by the cladding 42 is such that the fiber optic 22 has a low divergence as the light exit's the distal end 16. The core 40 is typically made of glass, e.g., silica quartz. The cladding 42 is typically made of silicone, plastic or silica. The core 40 and its cladding 42 have a combined diameter of less than about 0.5 millimeter to about 1.0 millimeter.

To protect the core 40 and its cladding 42, the fiber optic 22 normally also includes an external jacket 46 which surrounds the cladding 42 and is held in place by a resin coating 44. The external jacket 46 is usually made of a flexible plastic material such as poly(ethylene) or poly(tetrafluoroethylene). It provides a flexible and smooth surface allowing easy manipulation of the medical device. Fiber optic bundles are not preferred since the adhesive between individual fibers limits the amount of light which can be transmitted without melting of the bundle.

The fiber optic 22 should be flexible yet sufficiently resilient so that it is possible to push the fiber optic along a lumen. One such suitable fiber optic having a core diameter of 0.4 millimeters is marketed under the designation Med 400 by Quartz Products Corporation of Plainfield, N.J. Another suitable fiber optic is a 0.6 millimeter fiber optic commercially available under the designation HCT 600 from Ensign Bickford Co., Conn. The power that can be transmitted along fiber optic 22 varies with the size of the fiber. Utilizing the HCT 600 fiber optic a medical device embodying this invention can transmit as much as about 60 watts continuous power from a Nd:YAG laser source.

The bulbous element 18 irradiates both heat and light energy. Part of the light energy transmitted by fiber optic 22 is partially absorbed and converted by the element 18 into heat, and part of the light energy is emitted by the element 18 through aperture 24 as light. The relative proportions of the light energy that is radiated as light, or that is radiated and/or conducted as heat, are determined by the beam-splitter means 26.

The cross-sectional area of core 40 to fiber optic 22 is divided by the beam-splitter 26—essentially a concave notch extending into the core 40 of the fiber optic 22 at the position of aperture 24—into a part that is perpendicular to the axis of fiber optic 22 and another part that forms an acute angle to such axis. Substantially all of the light exiting the perpendicular part of fiber optic 22 at its beam-splitter means 26, i.e., exiting axially from fiber optic 22, is directed forward to be absorbed by the opposed light-receiving surface of bulbous element 18. The light-receiving surface of bulbous element 18 that is opposed to the distal end of fiber optic 22 is preferably treated, e.g., oxidized, in order to increase its coefficient of emissivity to about 0.95 or greater. This treatment further increases the absorption of light by the element 18. Alternatively, the light-receiving surface can be treated by being coated by a material such as lamp or carbon black having a high coefficient of emissivity.

The bulbous element 18 is preferably made of metal such as surgical stainless steel, but could also be made of a combination of thermally conductive and thermally insulating materials such as metal(s) and ceramic(s). The exterior surface of the bulbous element 18 is preferably coated with a non-stick or release surface such as poly (tetrafluoroethylene) to provide easy release from the tissue. Poly(tetrafluoroethylene) usually is used for operating temperatures below about 300 degrees C. The majority of the heat is generated by absorption of the laser light at the distal end of the bulbous element 18 where it is typically needed. Meanwhile, heat generation is minimized at the proximal portions of the element 18 where it could be detrimental to the fiber optic 22.

The bulbous element 18 has sufficient mass to avoid burn-through during use. However, the mass is not so great as to materially slow its heating rate. For this reason, it is advantageous to place the thickest portion of material in the forward portion of the element 18 where the radiant energy, e.g., light, impinges. The space between the distal end of the fiber optic 22 and the radiant energy receiving surface of the element 18 may fill with matter such as air or liquid during use. However, this matter is readily vented through aperture 24 due to expansion as a result of the heat generated.

The distal end portion of the bulbous element 18 is preferably generally rounded on its exterior surface (as illustrated) in order to facilitate pressing the element into and through softened body material while minimizing the risk of mechanical perforation. The bulbous element 18 can alternatively have other shapes as desired, including oblong or eccentric with respect to the axis of the fiber optic 22 or even generally crescent shaped. Such an eccentric or oblong shape can be rotated to generate an even larger channel through an obstruction. A crescent-shaped element also allows for viewing past the element.

The distal end of the fiber optic 22 is preferably spaced no more than two diameters of its core 40 away from the light-receiving surface of the bulbous element 18. Where the core 40 is about 0.5 millimeters, this spacing should be no more than about 1 millimeter. This relatively close spacing insures that Substantially all of the light emitted from the flat end surface of fiber optic 22 is received on the forward light-receiving surface of the bulbous element 18, and is not dispersed on the inside side walls of the cavity 20 between the distal end surface and the receiving surface.

Meanwhile, some light is diverted from optic fiber 22 by beam-splitter means 26 to be directly radiated from bulbous element 18. This radiation is in a direction substantially transverse to the axis of optic fiber 22. The beam-splitter means 26 is essentially an indentation or recess upon the fiber optic 22. The recess extends sufficiently deeply into the fiber core 40, as may be best observed in FIG. 5, so as to intercept a substantial portion of the light, and the light energy, which is transmitted along fiber optic 22 between laser light source 50 (shown in FIG. 1) and the fiber's distal end. The beam-splitter means 26 can be considered to create a lossy region, or region at which light is emitted, to the fiber optic 22.

The depth, and lineal extent, of the beam-splitter means 26 influences the total amount of the light energy that is radiated thereat. Typically, a variably predetermined portion of the light energy carried within fiber optic 22 may be radiated as light at the location of the beam-splitter means 26. The remaining light, and light energy, is transmitted to distal end of the optic fiber 22, radiated at that end, and absorbed by a light absorbent treatment or coating at the opposed surface of bulbous element 18. In this manner, the energy balance between localized heating performed by the element 18 due to emission of light versus local heating by thermally radiative and/or conductive paths may be predetermined in a controlled manner.

Alternative embodiments of the present invention, each having a different beam splitter means are illustrated in FIGS. 6–8. In particular, FIG. 6 shows a fiber optic 52 positioned within cavity 50 defined by bulbous element 58 and provided with a beveled or slanted end surface 56 that directs a portion of the transmitted laser energy outwardly through aperture 54 and at an acute angle to the major longitudinal axis of fiber optic 52.

Similarly, FIG. 7 shows fiber optic 62 terminating in a unitary spherical lens 66 that is positioned within bulbous element 68 and directs a portion of the transmitted laser energy outwardly via aperture 64.

FIG. 8 illustrates an embodiment where a separate spherical lens 76 is positioned at the very end of fiber optic 72 in cavity 70 of bulbous element 78 and directs a predetermined portion of the transmitted energy outwardly through aperture 74 while the remainder is absorbed by element 78 as heat.

FIGS. 9–11 illustrate embodiments where the beam splitter means is a fully or partially reflective surface, or mirror, that is positioned and sized so as to reflect a portion of the energy emitted from the end of the fiber optic outwardly through the aperture while the remainder is absorbed as heat. Within FIGS. 9–11 structural elements performing a similar function to elements previously shown in FIG. 5 generally have the same last two digits in their reference numerals.

FIG. 9 illustrates an embodiment where the aperture 224 to bulbous element 228 is substantially in the shape of a trough having an included angle that is typically a right angle and major surfaces that intersect at the bottom of cavity 220. The aperture 224 can alternatively be configured in the shape of a wedge, cone, pyramid, paraboloid or other surface or body that is relatively wider at the exterior surface of bulbous element 218 and relatively narrower at its regions intersecting cavity 220 and fiber optic 222 having core 240, cladding 242, resin coating 244 and external jacket 246. At least the wall, or surface, of aperture 224 opposite to the end of fiber optic core 240, and typically the entire surface of aperture 224, is reflective. The reflective surface 226 is preferably gold (Au), normally applied by plating. The preferred gold plating is that commercially available under the designation LASER GOLD (trademark of Epner Technology, Inc.). This is an ultra-high infrared reflectance gold coating provided by Epner Technology Incorporated, 25 Division Place, Brooklyn, N.Y. 11222. The preferred gold plating is reported by its manufacturer to exhibit an absolute spectral reflectance of better than 40% at 0.5 microns wavelength radiation, and better than 98% from 1.0 to 12.0 microns wavelength radiation. The radio of laser energy radiation R reflected by surface 226 and directed outwardly from aperture 224 versus the laser energy heat H absorbed within the bulbous body 218 may accordingly be made high, which is sometimes especially desired when the radiation energy R is not focused. The reflective surface 226 may alternatively be made of silver (Ag), mercury (Hg), or other energy-reflective materials, and may alternatively be created by gaseous deposition and other processes as well as by the process of plating.

FIG. 10 illustrates an embodiment where the reflective surface 226 of aperture 324 to bulbous element 318 is not coextensive with the beam of laser radiation emitted from the end of fiber optic 322 having core 340 cladding 342, resin coating 344 and external jacket 346. Instead, the reflective surface intercepts only a portion of the laser energy radiation emitted from the end of fiber optic 340, and substantially reflects this intercepted portion through aperture 324 to the exterior of bulbous element 318. A remaining portion of the laser energy radiation emitted from the end of fiber optic 340 impinges upon a portion of the wall of cavity 324 that is substantially non-reflective, and is absorbed within the bulbous element 218 as laser energy generated heat H. The size, location, and reflectivities of each of the reflective and non-reflective surfaces of aperture 324 may be adjusted to vary the relative proportion of laser energy radiation that is reflected through aperture 324 and that is absorbed as heat within bulbous element 318. The extent of the reflective surface 326, in particular may be adjusted by selectively masked plating, or by removal of a portion of the reflective surface, however applied, by mechanical means such as drilling or grinding. In this context of the selective adjustment of the extent of reflective surface 326, it should be understood that FIG. 10 is exemplary only, and that the exact contours of aperture 324 and the exact patterning and location of the reflective surface 326 could be subject to considerable variation depending upon exactly where, how, and to what extent energy is to be both thermally and radially delivered by medical devices in accordance with the present invention.

As an example of the considerable adjustment that may be made to the contours of the aperture, and to a reflective surface within such aperture that is employed as the beam splitter means, FIG. 11 illustrates an cavity 240 to a bulbous element 418 where a partially reflective surface 426 within the aperture 424 directs some of the laser energy radiation received from fiber optic 422 having core 440, cladding 442, resin coating 444 and external jacket 446, direction outwardly from the tip of bulbous element 418, while permitting some of this laser energy radiation to be absorbed by the bulbous element 418 as heat. The direction of laser energy in an outwardly direction is provided by a reflective surface 426, normally made of gold. Reflective surface 426 is concavely curved, typically as a spheroidal, ellipsoidal, or parabolic surface. The reflective surface can but need not cover the entire aperture 424 defining wall. The concave curvature, and spatial orientation, of reflective surface 426 around aperture 424 not only causes that the laser energy is reflected to the exterior of the tip of bulbous body 418, but that it may be focused to a desired degree as well. Both the outwardly direction and the focus, or partial focus, of laser energy radiation R can be particularly useful when the medical device in accordance with the invention is moved in a progression to heat and irradiate material within, or regions of, a patient's body.

FIG. 12 illustrates still another embodiment of the beam splitter means. The aperture 524 to bulbous element 518, and its reflective surface 526 is not coextensive with the entire end of fiber optic 522 having core 540 cladding 542, resin coating 544 and external jacket 546. The reflective surface 526 is instead oppositely disposed to but a portion of the area of the end of fiber optic core 540, and intercepts but a portion of the laser energy radiation emitted therefrom (similarly to the embodiment of FIG. 10). Only this intercepted portion of the laser energy radiation emitted from the end of fiber optic core 540 impinges on reflective surface 526 and thus is substantially reflected through aperture 524 to the exterior of bulbous element 518. A remaining portion impinges directly onto the bulbous element 518 where it is converted into heat H.

The device in accordance with the present invention permits the destruction of tissue or matter, such as the endometrium. When the bulbous element 18 is positioned relatively further or relatively closer to the tissue surface then the light beam emitted from aperture 24 will fall upon the tissue surface relatively more or less diffusely. Since the light beam produced by the bulbous element 18 is not directed into the tissue surface as a narrow, collimated beam, any destruction by high-temperature localized heating with intense light will not continue to transpire as the bulbous member 18 is retracted ever further away from the work surface.

In accordance with the present invention, a medical device is used for radiant heating of material within a patient's body, including the patient's own tissue, by irradiation with high intensity light. The light is sufficiently localized and sufficiently intense so as to cause sufficiently localized sufficiently high radiant heating of the material upon which the light selectively impinges so as to destroy such material. In accordance with the preceding discussion, this destruction will be understood not to transpire uncontrollably in all regions whereat the aperture distal end of the device is deployed, but to transpire only selectively along an arc in a direction that is substantially transverse to the long axis of the distal end of the device.

Further in accordance with the present invention, a medical device is used for conductively heating tissue of the patient's body, typically in regions local to the region(s) of tissue or material destruction by the high intensity light. This conductive heating typically occurs by direct thermal contact with an apertured distal end of the device while this end is heated sufficiently hot so as to cause localized cauterizing of the patient's bodily tissue with which it comes into contact. The heated device generally does not, however, produce heat that is either so localized or so high as that heat that is produced by the high intensity light radiation also emitted transversely from the device's distal end.

When the device of the present invention is utilized in an endometrial ablation procedure as previously discussed, it is especially useful for treating the portions of the endometrium '117 lining the side wall 121 of the uterus. Although not shown in the drawings, the optic fiber 22 and bulbous element 18 are inserted into the uterus by means of a hysteroscope as will be understood by those skilled in the art. Use of the element 18 will be under direct visual observation through the hysteroscope. The bulbous element 18 will be placed in contact with the endometrium 117 with the aperture 24 directed against the wall of the endometrium 117 as indicated in FIG. 1. The bulbous element 18 will then be slowly moved in a continuous motion so as to direct the heat energy therefrom across the entire portion of the endometrium lining the side wall 121.

The endometrium, when suitably prepared for this procedure, will have a thickness of approximately three millimeters. The laser energy exiting the aperture 24 and directed immediately against the endometrium has the ability to penetrate approximately five millimeters, thus penetrating the entire thickness of the endometrium through to the underlying muscle layers. Additionally, the somewhat greater area of less intense heating provided by conductive heating from the bulbous element 18 due to its contact with the endometrium 117 surrounds the localized area of heating provided through the aperture 24. It is the combined heating effect of both the laser energy exiting aperture 24 and the heat conducted from the heated mass of bulbous element 18 which destroys the endometrium.

Typically, the tissue of the endometrium is not vaporized, but instead is heated to an extent that it is completely penetrated by the high temperatures and is thus entirely destroyed or killed. After treatment, the endometrial tissue typically is reduced to a scar tissue on the myometrial or muscle layer of the uterine cavity.

Also, it is noted that on occasion an actively bleeding vessel will be encountered in this procedure. In such instances, it is sometimes preferable to rotate bulbous element 18 and contact the bleeding vessel with a back surface thereof to cauterize the vessel without applying direct laser energy.

The terms "laser energy" and "laser radiation" and "laser light" as used in this specification disclosure will be understood to encompass a broad range of radiation frequencies, characteristics, and energy densities. In particular, the device in accordance with the present invention will function satisfactorily with laser radiation of a broad frequency range of infrared (IR) and visible light. The laser radiation may be suitably produced by $CO_2$, Argon, Nd:YAG, and other types of lasers. Use of a beam splitter having a reflective surface plated with gold, as is preferred, is effective to accomplish the heating and radiating purposes of the invention over a great range of energy frequencies, characteristics, densities, and levels. For example, the device in accordance with the present invention is suitable for use with excimer laser radiation having a wavelength in the order 290–400 nm and power densities, pulse rates, and application times sufficient to cause multiphoton absorption and band breaking by coulomb repulsion rather than thermal destruction.

In accordance with the preceding discussion, further adaptations and variations of the present invention will be readily perceived by a practitioner the medical instrumentation arts. The size, aspect ratio, and contours of the bulbous element 18 can be adjusted as be suit the bodily cavity within which such member is employed. The focus of the emitted light can be varied in a sophisticated manner by incorporation of one or more lenses of standard design into aperture 24. Heat conduction within the bulbous element 18 may be varied by making the element out of both thermally conductive and thermally insulative material. The operation of that embodiment of the invention which has been taught in order to (i) produce a single, substantially directionally transverse, light beam and (ii) heat substantially omnidirectionally should be understood to be illustrative only, and not delimiting of the potential combinations of heating by irradiating with both light and heat that are subsumed within the present invention.

Therefore, the present invention should be interpreted in accordance with the language of the following claims, only, and not solely in accordance with that particular embodiment within which the invention has been taught.

What is claimed is:

1. A device for applying a laser energy beam to a selected body site, comprising:
    an elongated, laser energy transmitting conduit having a proximal end region with a proximal end defined thereon and a distal end region with a distal end defined thereon and defining a laser energy path; and
    a hollow element mounted on said distal end region of said conduit, said element including:
    a cavity defined therein within which said distal end region of said conduit is received;
    a closed distal end wall blocking any transmission of a laser energy beam distally from said element coaxial with said laser energy path at said distal end of said conduit;
    a laterally open aperture defined in said element and communicating with said cavity, said aperture being open to fluid communication from outside said element through said aperture into said cavity; and
    beam splitting means, disposed entirely within said cavity, for receiving laser energy transmitted through said conduit and for directing at least a first portion of said received laser energy as a laser energy beam exiting said element along a lateral beam path through said aperture.

2. The device of claim 1, wherein said beam splitting means includes a reflecting surface defined on said closed distal end wall and arranged to reflect said first portion of said received laser energy.

3. The device of claim 2, further comprising:
    a Nd:YAG laser energy source optically coupled to said proximal end region of said conduit; and
    wherein said reflecting surface is a gold surface which reflects substantially all of the laser energy incident thereon.

4. The device of claim 1, wherein said distal end of said conduit abuts said closed distal end wall.

5. The device of claim 1, wherein said distal end is slanted to direct said first portion of the received laser energy outwardly through said aperture.

6. The device of claim 1, wherein said distal end is rounded to direct said first portion of the received laser energy outwardly through said aperture.

7. The device of claim 1, wherein said closed end wall is spaced from said distal end of said conduit and from said selected body site when said element is placed in contact with said body site and with said aperture oriented toward said body site.

8. The device of claim 7, wherein said distal end is a lens unitary with said laser transmitting conduit.

9. The device of claim 7, wherein said distal end is slanted to direct said first portion of the received energy outwardly through said aperture.

10. The device of claim 7, wherein said distal end is rounded to direct said first portion of the received laser energy outwardly through said aperture.

11. A device for applying a laser energy beam to a selected body site, comprising:
    an elongated, laser energy transmitting conduit having a proximal end region with a proximal end defined thereon and a distal end region with a distal end defined thereon, and defining a laser energy path; and
    a hollow element mounted on said distal end region of said conduit, said element including:
    a cavity defined therein within which said distal end of said conduit is received;
    a closed distal end wall blocking any transmission of a laser energy beam distally from said element coaxial with said laser energy path at said distal end of said conduit;
    a laterally open aperture defined in said element and communicating with said cavity, said aperture being open to fluid communication from outside said element through said aperture into said cavity; and
    a reflecting surface defined on said closed distal end wall and arranged to reflect a portion of a laser energy beam exiting from said conduit as a lateral laser energy beam exiting said element along a lateral beam path through said aperture.

12. The device of claim 11, wherein said reflecting surface is gold.

13. The device of claim 12, further comprising:
    a Nd:YAG laser energy source optically coupled to said proximal end region of said conduit; and
    wherein said gold surface reflects substantially all of the laser energy incident thereon.

14. The device of claim 11, wherein said distal end of said conduit abuts said reflecting surface.

15. The device of claim 11, wherein said distal end is slanted to direct a portion of the transmitted laser energy outwardly through said aperture.

16. The device of claim 11, wherein said distal end is rounded to direct a portion of the transmitted laser energy outwardly through said aperture.

17. The device of claim 11, wherein said reflecting surface is spaced from said distal end of said conduit and from said selected body site when said element is placed in contact with said body site and with said aperture oriented toward said body site.

18. The device of claim 17, wherein said reflecting surface is curved.

19. The device of claim 17, wherein said distal end is a lens unitary with said laser transmitting conduit.

20. The device of claim 17, wherein said distal end is slanted to direct a portion of the transmitted energy outwardly through said aperture.

21. The device of claim 17, wherein said distal end is rounded to direct a portion of the transmitted laser energy outwardly through said aperture.

* * * * *

UNITED STATES PATENT AND TRADEMARK OFFICE
CERTIFICATE OF CORRECTION

PATENT NO. : 5,649,924
DATED : July 22, 1997
INVENTOR(S) : Royice B. Everett et al.

It is certified that error appears in the above-indentified patent and that said Letters Patent is hereby corrected as shown below:

Col. 11, line 27, "cavity 240" should be – aperture 424 –.
Col. 11, line 29, "aperture 424" should be – cavity 240 –.

Signed and Sealed this

Thirteenth Day of January, 1998

Attest:

BRUCE LEHMAN

Attesting Officer     Commissioner of Patents and Trademarks